United States Patent [19]

Nakata et al.

[11] Patent Number: 5,519,490
[45] Date of Patent: May 21, 1996

[54] CONDENSATION NUCLEUS TYPE DEVICE FOR COUNTING PARTICLES IN GAS UTILIZING HEATING MEANS ON THE CONNECTION PIPE AND MEASURING CHAMBER

[75] Inventors: Shigenori Nakata; Shintaro Sato; Seisaku Kamiya, all of Shizuoka, Japan

[73] Assignee: Ushiodenki Kabushiki Kaisha, Japan

[21] Appl. No.: 279,648

[22] Filed: Jul. 25, 1994

[30] Foreign Application Priority Data

Jul. 23, 1993 [JP] Japan ................................. 5-210977

[51] Int. Cl.⁶ .................................................. G01N 21/00
[52] U.S. Cl. .......................... 356/338; 356/246; 359/512
[58] Field of Search ................................ 356/335–343, 356/440, 246; 359/509, 512

[56] References Cited

U.S. PATENT DOCUMENTS

| | | | |
|---|---|---|---|
| 2,684,008 | 7/1954 | Vonnegut | 356/338 |
| 3,462,609 | 8/1969 | Beattie | 356/339 |
| 4,790,650 | 12/1988 | Keady | 356/337 |
| 4,914,297 | 4/1990 | Wieboldt et al. | 356/246 |
| 5,026,155 | 6/1991 | Ockovic et al. | 356/336 |
| 5,083,865 | 1/1992 | Kinney et al. | 356/338 |

*Primary Examiner*—Frank Gonzalez
*Assistant Examiner*—Jason D. Eisenberg
*Attorney, Agent, or Firm*—Sixbey, Friedman, Leedom & Ferguson

[57] ABSTRACT

A particle counting device is improved to prevent adhesion impurities that result from condensation of condensation vapor on optical systems and the like in a particle detection area or the like of a measuring device to detect particles contained in the atmosphere or in certain gases and using condensation nuclei. In particular, in a particle measuring operation in which, in a chamber for saturated vapor that contains a liquid that can condense at a room temperature, a gas is added to a saturated vapor, the gas is introduced into a condensation part that is at a room temperature, the vapor is condensed on the particles as nuclei, and in which the particles, in a connected particle detection area, are measured, a heater is provided to keep the temperatures of the detection area, the connection pipe and the nozzle at least at a temperature higher than or equal to the temperature of the condensation part, to prevent adhesion impurities of condensation vapor on optical systems and the like in the detection area.

3 Claims, 3 Drawing Sheets

CONDENSATION NUCLEUS TYPE DEVICE FOR COUNTING PARTICLES IN GAS UTILIZING HEATING MEANS ON THE CONNECTION PIPE AND MEASURING CHAMBER

BACKGROUND OF THE INVENTION

1. Field of the Invention

The invention relates to a device for counting fine particles that are in the atmosphere or contain certain gases. The invention further relates to a device for counting, in particular, fine particles that are in a clean room and contain a starting gas for the production of semiconductors.

2. Description of Related Art

It is generally known to utilize a measuring device that uses condensation nuclei as a device for counting fine particles that are suspended in the atmosphere or are contained in certain gases in a semiconductor production process.

In such a measuring device, gas that contains fine particles is introduced into a chamber for saturated vapor, so that it contains liquefied vapor. By cooling the gas containing liquefied vapor in a condensation part, and condensing the vapor on the fine particles as nuclei, an apparently enlarged fine grain size is obtained, due to which a subsequent detection process of the particles in a particle measuring part is made possible in a simple way and with increased accuracy.

In a conventional measuring device, alcohol is usually used as the liquid for condensation. Here, a condensation part is cooled to a temperature less than or equal to a room temperature and alcohol vapor is condensed. It is true that this process is for gases with a low flow rate, but for gases with a high flow rate it has a drawback that it needs a large cooling mechanism and thus is difficult to use in practice.

FIG. 1 illustrates a prior art measuring device using glycerine as the condensation liquid. In the illustration, a reference symbol 1 designates a chamber for saturated vapor, a reference symbol 2 designates a condensation part and a reference symbol 3 designates a particle measuring part using a light-scattering system.

Inside chamber 1 for saturated vapor, glycerine 4 is encapsulated as the liquid for condensation, and it is heated by a heating means 5 placed under it. Condensation part 2 connected to this chamber 1 for saturated vapor consists of narrow pipes 6 and is exposed, without a special cooling means, to a room temperature.

Attached particle measuring part 3, to which condensation part 2 is connected by a connection point 25, has the same arrangement as a usual air counter and is provided, on a side with a light source, with an optical system that consists of a lamp or laser 7, a lens 24 for light collection, a slit 9 and a projection lens 10 and, on a light collection side, with an optical system that is placed opposite the above-described optical system, and consists of a convex lens 11 and a device 12 for fight collection.

Gas containing fine particles is introduced out of an inlet 1 a into chamber 1 for saturated vapor, which is filled with a saturated vapor of glycerine heated by heating means 5. Next, the introduced gas is mixed with a glycerine vapor in this chamber 1 for saturated vapor.

Next, the mixed gas is fed to condensation part 2. In narrow pipes 6 of condensation pan 2, whose temperature is about at a room temperature, the glycerine vapor grows by condensation on the fine particles contained in the gas as nuclei.

Fine particles grown like this are optically measured in connected particle measuring pan 3. Particle measuring part 3 has, as described above, an open design in which no partition is placed between a gas flow line and the optical systems, such as lenses and the like. Here, light from laser 7 is focused using the optical systems and irradiates a detection area. Scattered light produced when the grown particles in the mixed gas pass through the laser light is detected by convex lens 11 in the device for light collection 12. In doing so, a penetration of directly projected light from a lamp into the optical system on the light-collecting side is prevented by a beam stopper 17.

Such a prior art device is known from the references cited below:

A counting of particles using condensation nuclei is described in Japanese laid-open specification SHO 57-42839 entitled "Process for counting superfine particles and device for performing the process". A counting of particles using the light-scattering system is described in Japanese laid-open specification SHO 64-53132 entitled "Particle detector," in Japanese laid-open specification SHO 64-53131 entitled "Particle detector" and in Japanese laid-open specification SHO 55-39772 entitled "Particle measuring pan."

Because of the fact that, in contrast to using alcohol vapor at a normal temperature, condensable glycerine is used, the above-described prior art requires no special cooling means in the condensation part and is suitable for detecting particles in gas with a high flow rate.

The temperature of the condensation part is exposed to room temperature and is not regulated. But, it rises slightly above room temperature as a result of the high temperature of the mixed gas, specifically by about 5° to 15° C. above a room temperature of about 25° C. This means that the attached particle measuring part, a connection pipe or nozzle placed between the particle measuring part and the condensation part and whose temperature is about at a room temperature, has a lower temperature than the temperature of the condensation part.

As a result of this, the glycerine vapor condenses on the particle measuring part, the connection pipe or nozzle, and adheres to the optical systems placed in the area. Especially in the gas flow line, which consists of the particle measuring part, the connection pipe and the nozzle, as a result of its design in which there is no partition to the optical systems that focus the laser light, the above-described problem appears extraordinarily frequently. After a long period, such a phenomenon has a negative influence on measuring accuracy, such as degradation of sensitivity, frequent miscounting and the like.

The above-described drawback, i.e., condensation of the vapor on the measuring part, hardly occurs when using alcohol as the condensation liquid, because in doing so the temperature of the condensation part is at a low temperature of less than or equal to room temperature and the measuring part is at a room temperature and thus has a higher temperature than the condensation part. Further, as a result here of a rather high vapor pressure of alcohol at a room temperature, in case the condensed liquid of alcohol adheres to the measuring part, the condensed liquid of the alcohol can be brought back into the previous state and reused by letting it stand for a certain time or by letting gas flow over it.

In contrast, when using glycerine, condensed liquid of the glycerine that once adhered to the measuring part hardly evaporates at a room temperature, since its vapor pressure at room temperature is extremely low and thus is difficult to bring back into the previous state without performing a process such as separation or the like.

SUMMARY OF THE INVENTION

In view of the above-described defect, a primary object of the present invention is to provide a measuring device which uses a liquid that can condense at a normal temperature and which is able to perform a measuring operation with a condensation part at a temperature of 30° to 45° C., which is higher than a room temperature. In particular, a measuring device is proposed which utilizes glycerine, triethylene glycol, diethylene glycol or the like as a condensation liquid.

This object is achieved according to a preferred embodiment of the invention by a device for particle counting that has a chamber for saturated vapor that contains liquid that can condense at a room temperature and in which, by heating this liquid, a saturated vapor is produced, a condensation part in which a gas containing particles is mixed with the above-described saturated vapor and, by condensation of this mixed gas, particles are made to grow, and a measuring part for counting the above-described grown particles. A heating means is attached to the above-described measuring part by which the temperature of the measuring part is raised to at least the temperature of the condensation part.

The object is further achieved according to the invention by placing, between the condensation part and the measuring part, a connection pipe and/or a nozzle that is also provided with a heating means by which the temperature is raised to at least the temperature of the condensation part.

The object is further achieved by placing, in the measuring part, for counting particles, a measuring device using a light scattering system.

The object is furthermore achieved by placing, in the measuring part, a flow cell that is optically transparent and through which the particle-containing gas passes and by having an external heating means at least partially heat the flow cell.

With the particle-counting device according to the invention, the mixed gas produced in the chamber for saturated vapor is introduced into the condensation part and grows as nuclei by condensation on the fine particles it contains. It is true that the condensation part, without temperature regulation, is exposed to a room temperature, but because of the high temperature of the mixed gas, it has a temperature higher than the room temperature. But, since the measuring part, connection pipe or nozzle have a heating means for heating at least to the temperature of the condensation part, no condensation results due to the temperature of this part being lower than the temperature of the condensation part.

These and further objects, features and advantages of the present invention will become apparent from the following description when taken in connection with the accompanying drawings which, for purposes of illustration only, show several embodiments in accordance with the present invention.

DETAILED DESCRIPTION OF THE PREFERRED EMBODIMENT

Figure 1:
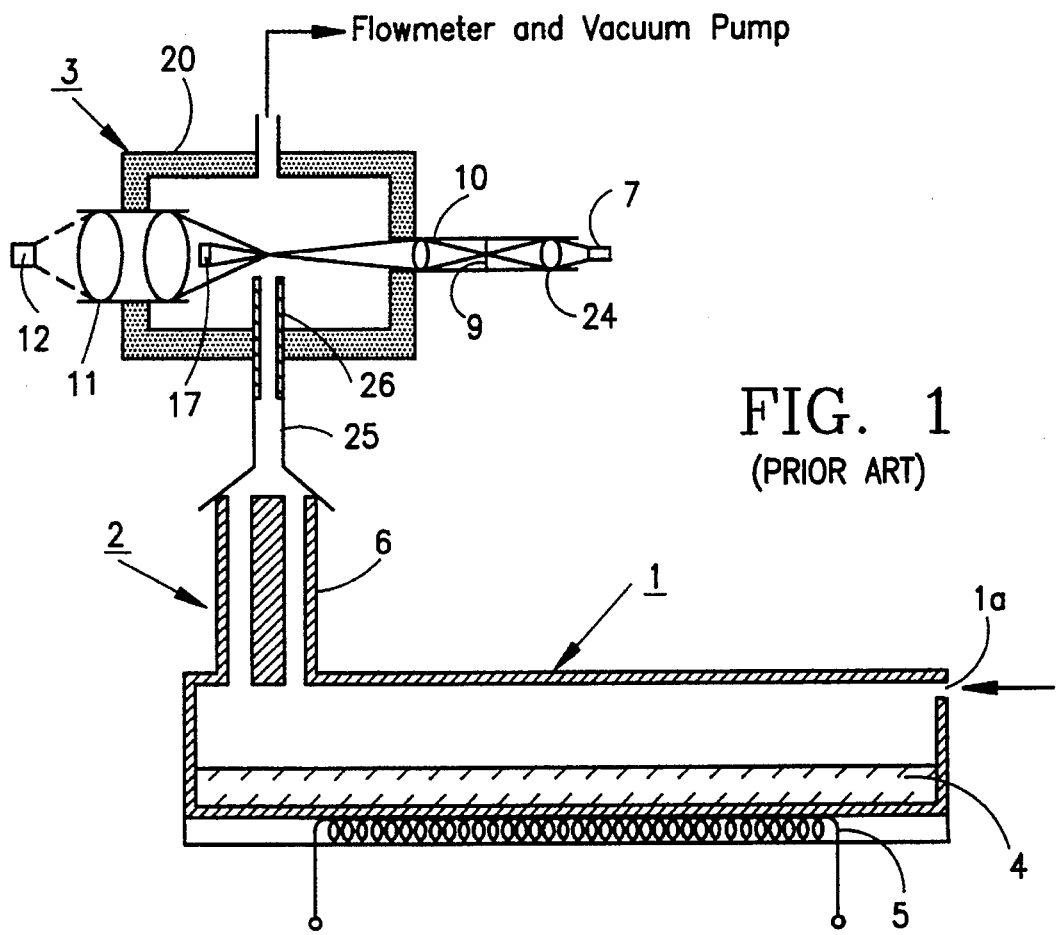
FIG. 1 is a diagrammatic representation of a conventional particle detector using condensation nuclei.
Figure 2:
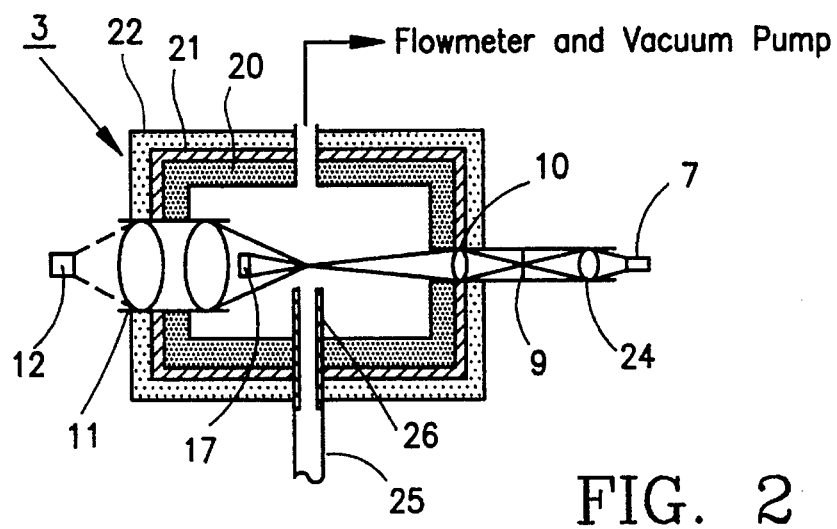
FIG. 2 is a diagrammatic representation of essential parts of the particle detector according to the invention.

FIG. 2 diagrammatically shows a particle measuring part of the device, according to the invention, for particle counting using condensation nuclei. In the representation, neither the chamber for saturated vapor nor the condensation part are explained and reference can be made to the description of these elements 1, 2 in connection with FIG. 1, the same reference numerals used in FIG. 1 being carried over into FIG. 2 to facilitate an understanding of the relationship of the described parts of the device according to the invention to those of the prior art device.

A particle measuring part 3 has a chamber 20, outside which a heating means 21 is installed. Heating means 21 is, for example, a silicone-rubber heating device or a "sheath heater" and is regulated by an externally attached temperature regulator. On an outer side of this heating means 21, a thermal insulating material 22, such as polyurethane or the like, is wrapped. Using a temperature detection means of the condensation art, which is not represented in the figure, the heating means 21 can further be advantageously regulated according to the detected values.

However, not only can a heating means 21 that completely heats the particle measuring part 3 be used, but also a heating means can be used which only partially heats the particle measuring part 3.

Further, as the heating means 21, a lamp such as a halogen heating device or the like can be used.

Figure 3:
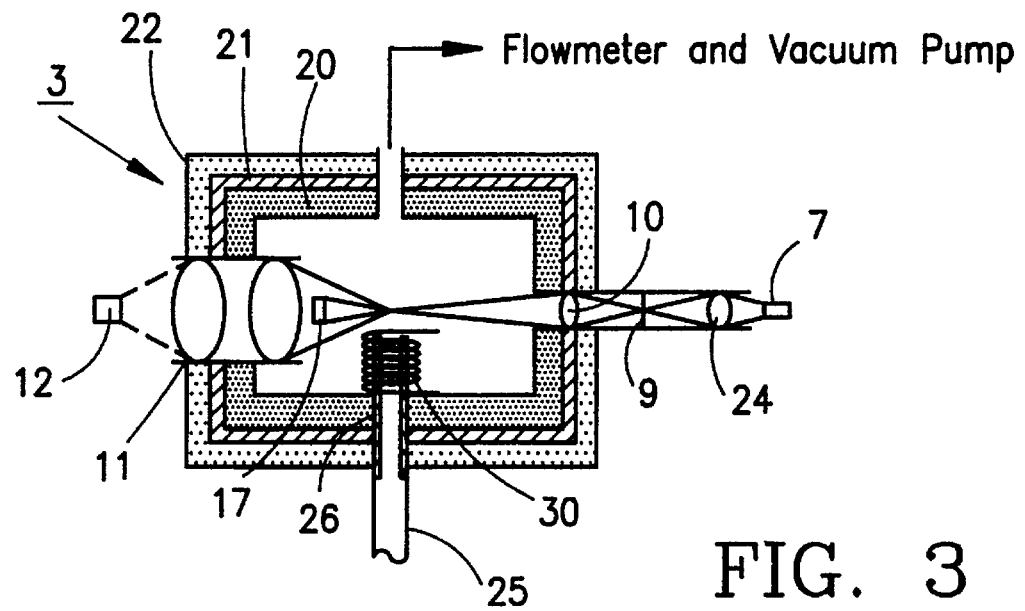
FIG. 3 is a diagrammatic representation of essential parts of another embodiment of the particle detector according to the invention.

FIG. 3 also illustrates a particle measuring part of the device, according to the invention, for particle counting using condensation nuclei. Fine particles grown by condensation that are fed out of a connection pipe 25 are introduced by a nozzle 26 into a chamber 20.

This embodiment is characterized in that, not only is heating means 21 placed in chamber 20, but also a heating means 30 comprised of, for example, a heating device using a chrome nickel wire, is placed in a part of nozzle 26. This measure by which nozzle 26 is also provided with heating means 30 makes it possible that each part on which the glycerine vapor might slightly condense is subjected separately in each case to temperature regulation. Thus, the incidence of condensation can be largely prevented. If sufficient temperature regulation can be performed using heating means 30, heating means 21 placed in chamber 20 is not absolutely necessary.

Figure 4:
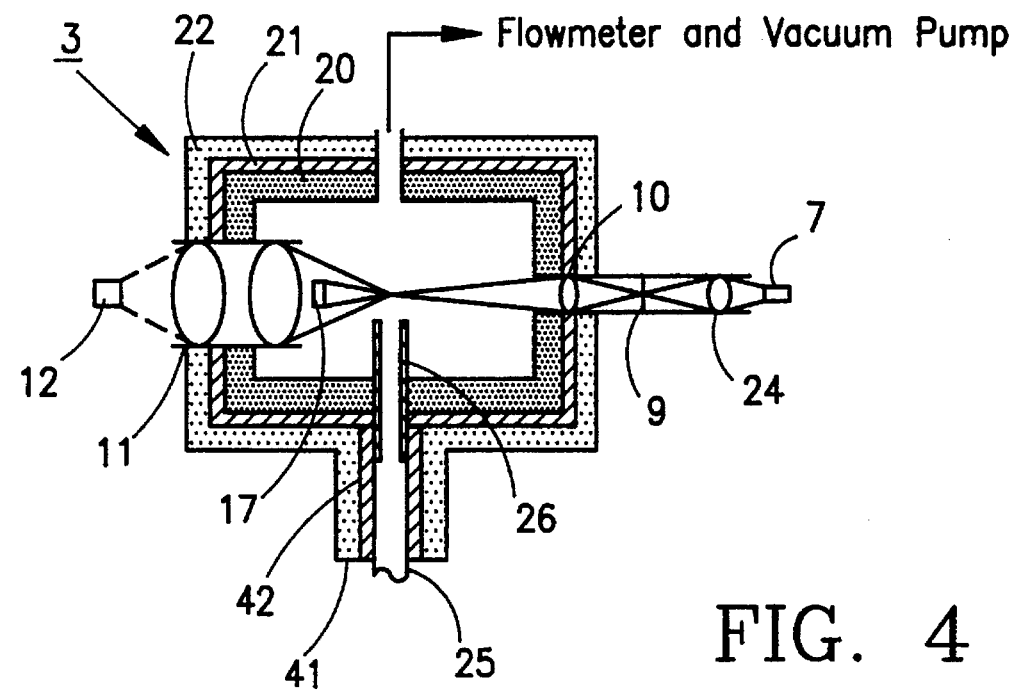
FIG. 4 is a diagrammatic representation of essential parts of yet another embodiment of the particle detector according to the invention.

FIG. 4 shows another embodiment of a particle measuring part of the device, according to the invention, for particle counting using condensation nuclei. In this embodiment, not only is heating means 21 placed in chamber 20, but a heating means 41, comprised of a silicone-rubber heating device or "sheath heater," is also placed on part of the connection pipe 25.

This measure, by which a heating means 41 is also placed on connection pipe 25, makes it possible that each part on which glycerine vapor might slightly condense is subjected separately in each case to temperature regulation. Thus, the incidence of condensation can be largely prevented.

Further, a design in which heating means 41, combined with heating means 21 installed in chamber 20, is attached, is not absolutely necessary, and heating means 41 alone can be used. It is also possible to arrange heating means 41, combined with connection pipe 25, and nozzle 26 shown in FIG. 3 can be provided with heating means 30.

The measuring device according to the invention further makes it possible to measure fine particles with a diameter of about 0.01 microns when they have reached a diameter of about 0.5 to 1.0 microns because of condensation growth.

The temperature of the mixed vapor is, for example, when using glycerine as the condensation liquid, about 65° C. This means that mixed, vapor with such a high temperature is brought, by condensation in the condensation part 2, to grow on the fine particles as nuclei. In doing so it can happen that, only because of the measure of exposing the mixed vapor to room temperature, an insufficient condensation growth is performed in a simple way.

But, in this case, cooling air can be blown into the condensation part 2 or a cooling fin can be installed on an external surface of the condensation pipe 6, to achieve sufficient condensation growth. According to the invention, also with such a special arrangement for cooling in the condensation pipe 6, because of the respective temperature of the condensation pipe 6, an advantageous heat regulation of the particle measuring pan 3 or the like can be achieved.

Figure 5:
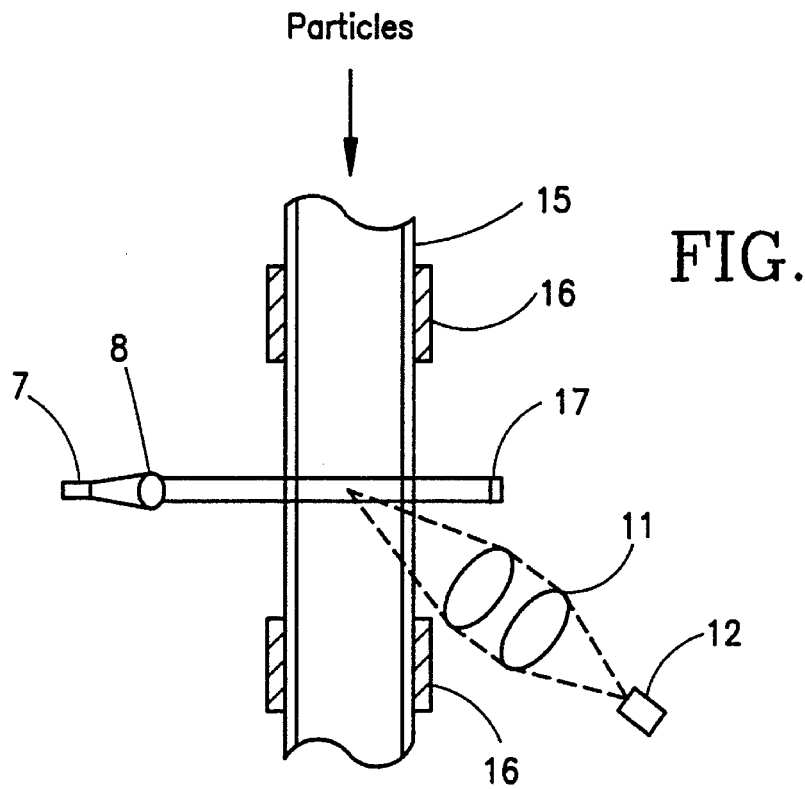
FIG. 5 is a diagrammatic representation of essential parts of the particle detector according to the invention.

FIG. 5 shows another embodiment of particle measuring part 3. In chamber 20, placed at a point corresponding to a gas flow line, there is a flow cell 15 that is comprised of an optically transparent pipe, such as quartz or the like. Particles grown by condensation and introduced from the connection pipe 25 and nozzle 26 pass through it.

Scattering light from a laser that irradiates this flow cell 15 in a perpendicular direction is produced by the particles.

Flow cell 15 is provided with a silicone rubber heating device as heating means 16. This heating means 16 must not be placed at the detection area; but, it is, however, desirable to put it near the detection area so long as it does not disrupt detection of the scattered light.

The placement of flow cell 15 makes it possible, in the case where the flow cell becomes unusable because of adhesion of condensed liquid, to resolve the problem by simply exchanging the flow cell or removing it for cleaning thereof. This is possible because the mixed vapor is completely separated from the laser, the light collecting device, the optical lenses and the like.

Further, the design using separate temperature-sensitive parts, such as laser and the like, makes it possible to have heating at a high temperature, which increases the effect of preventing adhesion of condensed liquid on the flow cell.

Further, also in case of adhesion of condensed liquid on the flow cell, the flow cell can be cleaned without exchanging by heating it until it reaches a high temperature and accelerating vaporization, if only a small amount of condensed liquid has adhered.

After light focusing, the light from laser 7 irradiates the detection area via a collimation lens 8 through the flow cell 15. The scattered light of the particles is detected through convex lens 11 by a photodetector 12.

It is true that heating means 16 heats flow cell 15 itself. But, by thermal conduction of flow cell 15, the temperature in the detection area, which is an internal chamber of flow cell 15, and of the area through which the scattered light passes, can also be kept at a temperature which is greater than or equal to the temperature of the condensation part 2.

Figure 6:
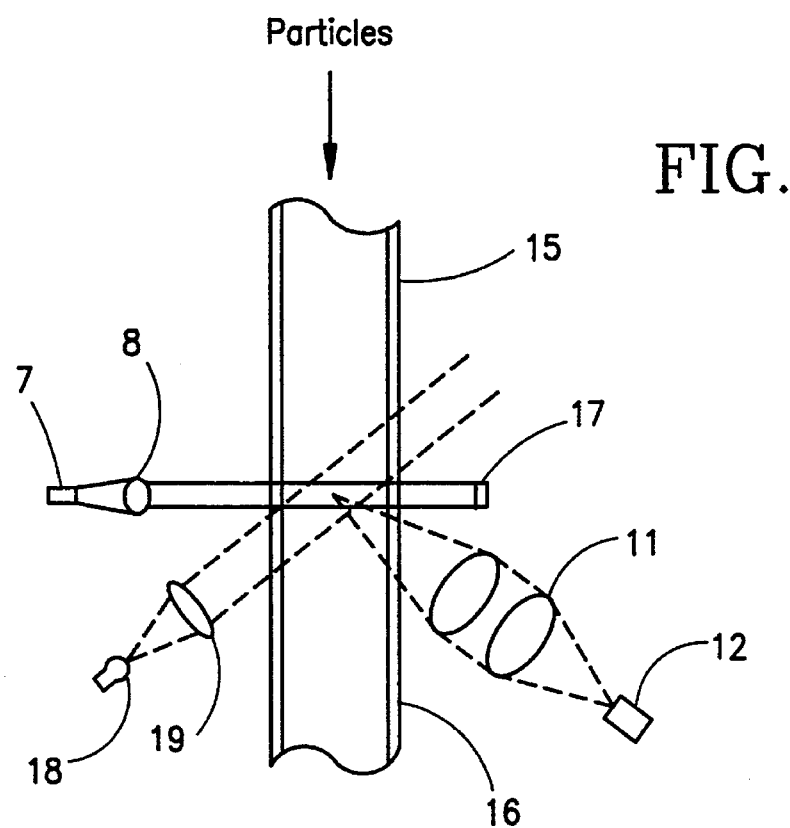
FIG. 6 is a diagrammatic representation of essential parts of the particle detector according to the invention.

FIG. 6 shows yet another embodiment of the particle measuring part using flow cell 15. In FIG. 6, instead of a heating device, a heating lamp 18 is placed outside flow cell 15. A halogen heating lamp is used for heating lamp 18. With lamp 18, it is desired that the surface of the lamp be coated with a material having a strong far infrared radiation pattern to filter the radiation to avoid an emission of the lamp light at the laser light wavelength for particle detection. It is further desired to focus the light from heating lamp 18 by a mirror or a lens 19 and to irradiate only the area requiring heating.

A simpler design is achieved by these measures, by which heating outside flow cell 15 is performed by heating lamp 18 and impurities produced by adhesion of glycerine vapor on an internal side of flow cell 15 are prevented.

Because of the invention the particle measuring part, the connection pipe or nozzle placed between the particle measuring part and the condensation part, can be heated to at least the temperature of the condensation part. In this way, adhesion of the glycerine vapor on the optical systems in the vicinity resulting from condensation, and thus an influence on the measuring accuracy, can be prevented.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. A device for counting particles using a condensation nucleus method comprising a chamber for producing a saturated vapor and containing a liquid which is condensable at room temperature, first heating means for producing the saturated vapor from said condensable liquid, and a condensation part for receiving the saturated vapor and a particle-containing gas and for producing a saturated gas mixture from said saturated vapor and particle-containing gas; wherein said condensation part has means for maintaining it at a temperature at which condensation of the saturated vapor of said gas mixture and growth of the particles of the particle-containing gas take place; and wherein a separate measuring part for counting particles grown in said condensation part is provided, said measuring part being connected to said condensation part by a connection pipe for admitting said particles grown into said measuring part which is provided with a second heating means for raising the temperature of said connection pipe to at least the temperature of the condensation part; and wherein the measuring part comprises a light-scattering system for measuring the particles grown based on an intensity of light scattered by the particles grown and is provided with a third heating means for maintaining the measuring part at least at the temperature of the condensation part.

2. A device for counting particles according to claim 1, wherein a flow cell is provided in the measuring part, said flow cell being optically transparent and being arranged to receive said particle-containing gas; and wherein an external heating means is arranged to at least partially heat the flow cell.

3. A device for counting particles according to claim 1, wherein the measuring part comprises a nozzle on said connection pipe; and wherein a fourth heating means is positioned on said nozzle for raising the temperature of said nozzle to at least the temperature of the condensation part.

* * * * *